(12) United States Patent
Lim et al.

(10) Patent No.: US 7,918,778 B2
(45) Date of Patent: Apr. 5, 2011

(54) GYNECOLOGICAL BRACHYTHERAPY APPLICATOR AND SYSTEM

(75) Inventors: Alex Lim, Santa Clara, CA (US); Paul A. Lovoi, Saratoga, CA (US); Heike Hausen, Menlo Park, CA (US); Daren L. Stewart, Belmont, CA (US)

(73) Assignee: Xoft, Inc., Sunnyvale, CA (US)

( * ) Notice: Subject to any disclaimer, the term of this patent is extended or adjusted under 35 U.S.C. 154(b) by 0 days.

(21) Appl. No.: 12/074,468

(22) Filed: Mar. 3, 2008

(65) Prior Publication Data

US 2008/0167514 A1  Jul. 10, 2008

(51) Int. Cl.
*A61N 5/00* (2006.01)
(52) U.S. Cl. .......................................................... 600/6
(58) Field of Classification Search .................. 600/1–8, 600/30; 604/20, 21
See application file for complete search history.

(56) References Cited

U.S. PATENT DOCUMENTS

| | | | |
|---|---|---|---|
| 3,872,856 A | 3/1975 | Clayton | |
| 4,554,909 A | 11/1985 | Torres | |
| 5,653,683 A | 8/1997 | D'Andrea | |
| 5,720,717 A | 2/1998 | D'Andrea | |
| 5,913,813 A | 6/1999 | Williams et al. | |
| 5,947,891 A | 9/1999 | Morrison | |
| 6,036,631 A | 3/2000 | McGrath et al. | |
| 6,338,709 B1 | 1/2002 | Geoffrion et al. | |
| 6,352,501 B1 | 3/2002 | Urick | |
| 6,390,968 B1 | 5/2002 | Harmon | |
| 6,413,203 B1 | 7/2002 | Sahatjian | |
| 6,413,204 B1 | 7/2002 | Winkler et al. | |
| 6,641,518 B2 | 11/2003 | Wolfson et al. | |
| 6,648,810 B1 | 11/2003 | Tenerz et al. | |
| 6,746,465 B2 | 6/2004 | Diederich et al. | |
| 6,799,075 B1 | 9/2004 | Chornenky et al. | |
| 7,338,430 B2 * | 3/2008 | Lim et al. ..................... 600/7 |
| 2001/0016725 A1 | 8/2001 | Valley et al. | |
| 2003/0153803 A1 | 8/2003 | Harmon | |
| 2004/0260142 A1 | 12/2004 | Lovoi | |
| 2005/0080340 A1 | 4/2005 | Stewart et al. | |
| 2005/0101824 A1 | 5/2005 | Stubbs | |
| 2005/0251108 A1 | 11/2005 | Frassica | |
| 2008/0009659 A1 | 1/2008 | Smith et al. | |

* cited by examiner

*Primary Examiner* — Charles A Marmor, II
*Assistant Examiner* — Christine D Hopkins
(74) *Attorney, Agent, or Firm* — Thomas M. Freiburger

(57) ABSTRACT

A vaginal brachytherapy applicator is versatile to different anatomies and more comfortable to the patient than prior applicators. An inflatable balloon on a shaft may be inelastic or elastic. In one embodiment the shaft is rotatable relative to the balloon for enabling a ring or band of dose delivery, for versatility in radiation placement. Alternatively, the source can be rotated and pulled back within a stationary shaft. An adjustment is provided for reducing the length of balloon that inflates, to accommodate different anatomies and positions. Although isotope radiation sources can be used in the applicator, an electronic source is preferred, and the system and method include procedures for using the applicator with an electronic source.

2 Claims, 7 Drawing Sheets

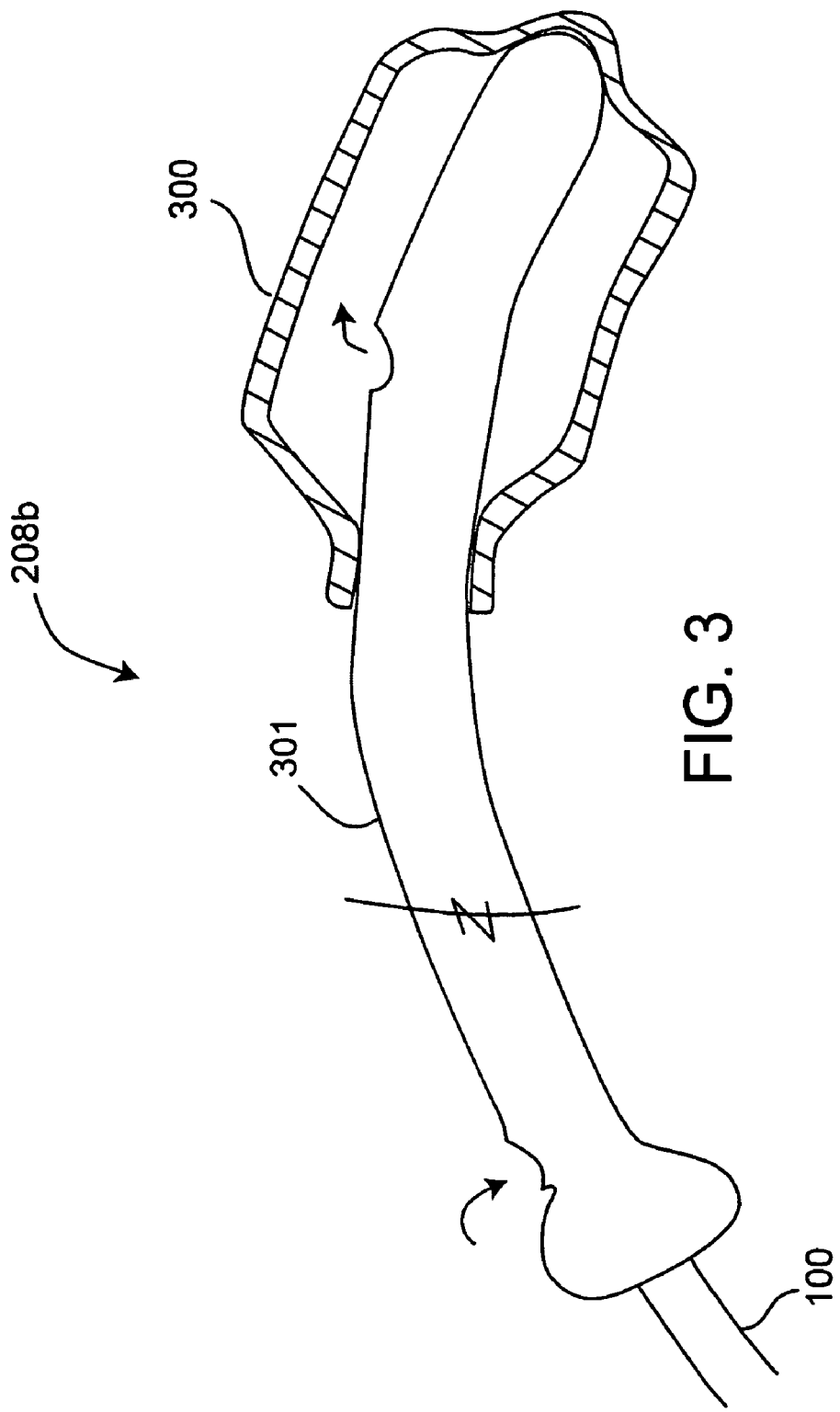

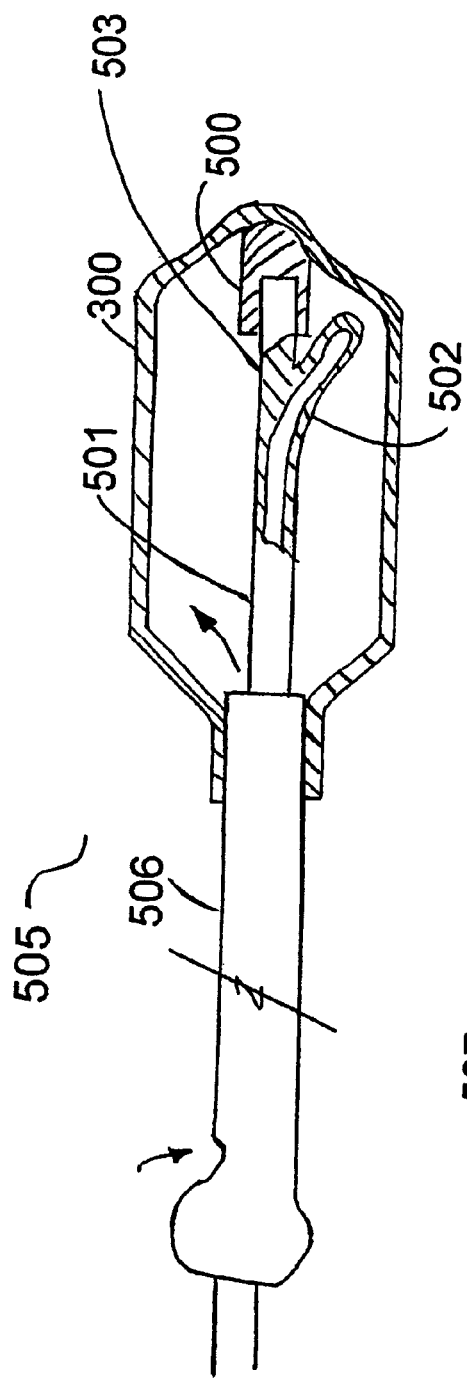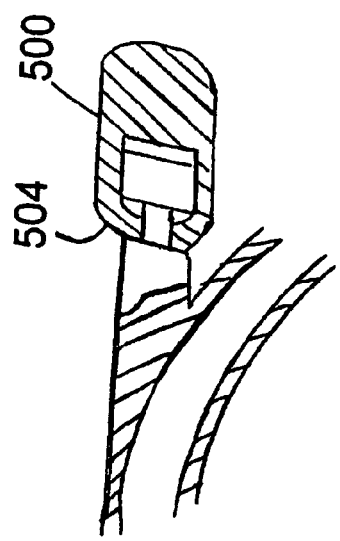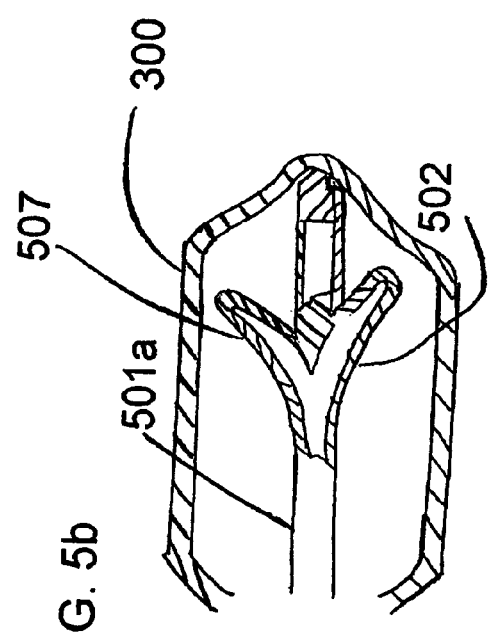

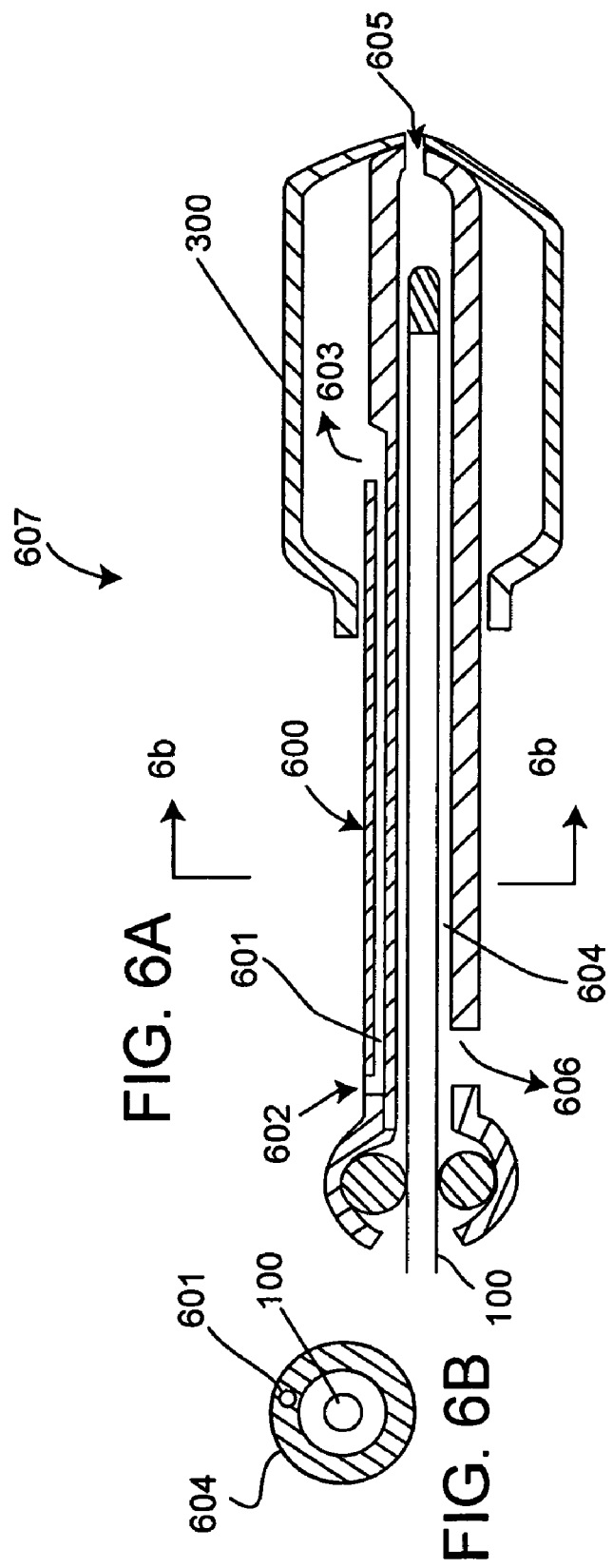

GYNECOLOGICAL BRACHYTHERAPY APPLICATOR AND SYSTEM

BACKGROUND OF THE INVENTION

This application claims benefit of application Ser. No. 11/323,346, filed Dec. 30, 2005, now U.S. Pat. No. 7,338,430, issued Mar. 4, 2008, which was a continuation-in-part of application Ser. No. 10/464,140, filed Jun. 18, 2003.

This invention concerns radiation therapy, especially for treating tissue which may have malignancies, and in particular the invention relates to an applicator for delivering radiation to a vaginal cavity and/or to adjacent tissue post full/partial hysterectomy for surgical treatment of cancer. Treatment of endometrial cancer is encompassed by the invention.

Vaginal or endometrial cancer, or malignancies in adjacent tissues, have been treated by applicator cylinders designed to receive radioactive isotopes. Applicators of this general type are shown, for example, in U.S. Pat. Nos. 5,913,813 and 6,413,204. Even though the applicator cylinders are sized to the vaginal cavity or adjacent anatomy, these types of applicators have often been uncomfortable or painful on insertion and once inserted have failed to provide a good fit. Ideally, the tissue should be positioned closely against the applicator. The conventional applicator can cause discomfort, inconvenience and less than ideal treatment in many cases. Such devices also lack flexibility in dose delivery profile. Basically, prior art applicator cylinders have included a straight lumen down the center through which radioactive seeds were delivered.

SUMMARY OF THE INVENTION

The invention is an improved applicator for gynecological brachytherapy, more comfortable to the patient on insertion and in use, more versatile, and optimally with capability of rotating a radiation emitting device to produce a ring or band of irradiated tissue. The device has a main shaft to which is secured or connected an inflatable balloon surrounding the distal end of the shaft which will be inserted into the body of the patient. The shaft may have alternate configurations for variations in positioning a radiation source, or to accommodate a range of therapeutic treatments. Multiple guides for the radiation source(s) can be included, as also disclosed in copending application Ser. No. 10/464,140, incorporated fully herein by reference. The invention encompasses use of isotopes, but especially in preferred embodiments, embraces application of variable voltage and/or current to a switchable electronic miniature x-ray source (or to several sources) in order to optimize a treatment plan. Also, the system can employ feedback control in real time, to feed actual sensor-determined radiation values back to a controller to adjust and control the dose delivered by the electronic radiation device, to achieve a desired dose profile even in a cavity of irregular shape, utilizing directionality of radiation if necessary.

In one preferred implementation of the invention, a brachytherapy applicator comprises an inflatable balloon, with a shaft extending into the interior of the balloon, the shaft having a conduit for inflating the balloon by admitting fluid to the balloon's interior. A source of ionizing radiation for delivery of radiation is affixed to or retained at the distal end of a flexible catheter or a rigid wand, depending on the application at hand. The source catheter or wand is contained in or received in the applicator shaft and is guided into the space within the balloon. A fluid tight seal, such as by a bonded joint, is provided at the proximal end of the balloon to seal the balloon against the exterior of the shaft in this embodiment. At the interior of the proximal end of the shaft in this preferred embodiment, an O-ring seal seals the shaft to the exterior of the flexible catheter or rigid wand comprising the radiation source, permitting rotation as well as axial movement between the radiation source structure and the shaft without substantial fluid leakage.

The radiation source may be omni directional or direction specific to suit the application. In one embodiment a radio opaque source guide including a radiation window is provided between the shaft and the source catheter or wand to control the directionality of emitted radiation. The radiation source and source guide can be rotatable within the shaft without substantial loss of fluid from the interior of the balloon. A preferred form of the shaft is configured to allow pullback of the radiation source.

In use, the balloon on the shaft is placed in a gynecological cavity with the balloon deflated, the radiation source is inserted, and once in place, the balloon is inflated (in some embodiments the balloon can be put in place and inflated before the radiation source is inserted). With the ionizing radiation source in the shaft, the source can be rotated and/or moved axially by machine or by hand, manipulated from a position outside the patient to control the locations from which the radiation is to be emitted, and the directions in which the radiation is to be directed.

In the various applicator embodiments described, the distal end of the applicator shaft is preferably affixed to the distal end of the balloon, or includes a rotary bearing connecting the distal end of the shaft to the distal end of the balloon, so as to permit rotation while supporting the balloon on the shaft.

The distal end of the shaft or source guide (most remote from the controller as used herein) in one embodiment is bent to an oblique angle for emitting the directional radiation outwardly and axially from the applicator, with capability of rotating the shaft relative to the balloon; alternatively, directional radiation can be emitted from a straight shaft located generally centrally. The shaft of an applicator refers to that element of the applicator that connects to the balloon (rotationally or not) and which provides an internal lumen or guide for receiving the radiation source.

Another preferred feature of the invention is a means for adjusting the size of the inflated portion of the balloon. This can be accomplished using a slidable tubular sheath over the shaft that slides axially relative to the shaft, and when moved forward (distally), covers a desired portion of the balloon from the proximal end of the balloon so as to prevent or limit expansion of the balloon in the sheath-covered portion. The expanded length of the balloon is thus limited as desired. This adjustment accommodates different anatomies of different patients, as well as adjusts for different regions within the anatomy.

As noted above, the source of ionizing radiation in a particular preferred embodiment is an electronic switchable x-ray source, which is not only switchable on/off but is adjustable as to voltage and current, and thus as to x-ray penetration depth and cumulative dose delivered. This affords attaining a much more accurate delivered dose profile than can be obtained using prior art methods since the control of radiation allows accommodation of differences in distance from source to tissue and differences in dose delivered to different tissue regions. It also provides a more flexible and anatomy-conforming applicator.

When the anatomy demands, or when the morbidity requires, an embodiment is provided in which the shaft and other elements of the apparatus can be bent to facilitate entry into the uterus after dilation. For example, the shaft may be formed in a continuous curve, or may comprise a deformable element, for example annealed metal, which may be formed by the doctor to accommodate the patient's anatomy.

It is thus among the objects of the invention to greatly improve efficiency, reliability, versatility, patient comfort and dose accuracy in brachytherapy radiation within the vaginal cavity and adjacent anatomy. These and other objects, advantages and features of the invention will be apparent from the following description of preferred embodiments, considered along with the accompanying drawings.

DESCRIPTION OF THE DRAWINGS

FIG. 3 is a side elevation view of a curved embodiment of the applicator similar to that of FIG. 1, in partial cross section.

FIG. 5 depicts a side view of an alternate embodiment of the invention in partial cross-section, comprising a shaft with a curved channel to direct radiation distally and rotatably about the shaft axis.

FIG. 5a is a side view of an alternative bearing configuration in partial cross section.

FIG. 5b is a view similar to FIG. 5 but showing another embodiment.

FIGS. 6a and 6b show side and axial views in cross-section of apparatus of the invention that includes suction applied to the distal end of the applicator to draw of accumulated fluid or exudate.

DESCRIPTION OF PREFERRED EMBODIMENTS

Figure 1:
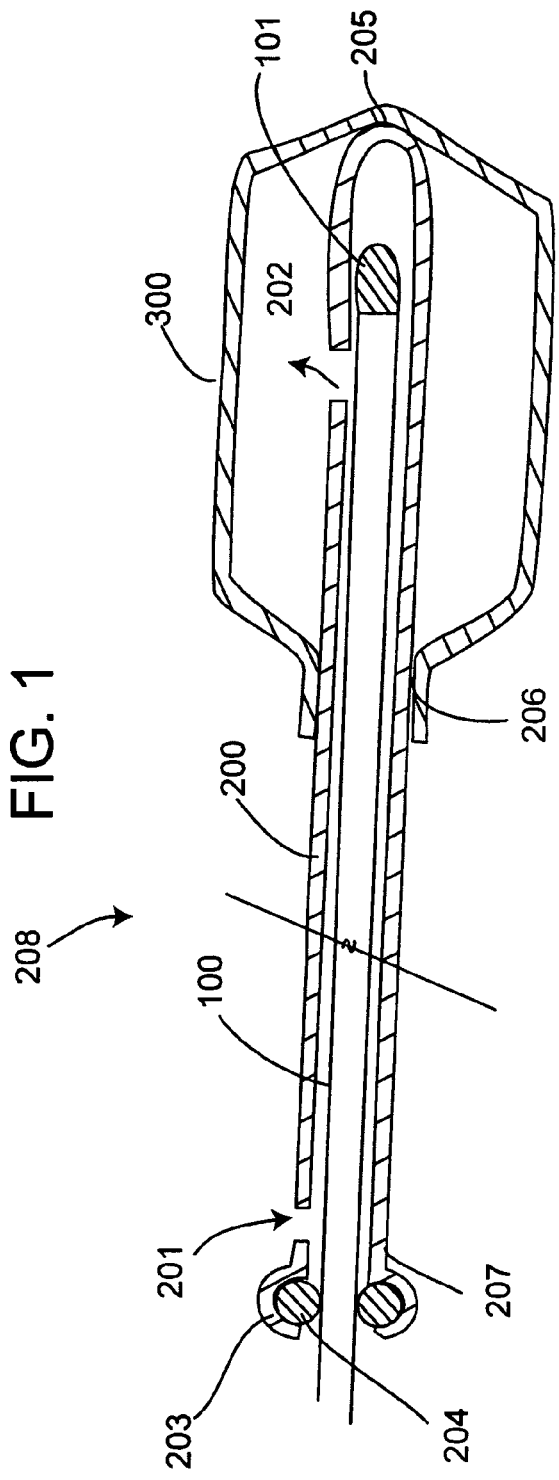
FIG. 1 is a side view in cross-section of a preferred embodiment of the invention.

FIG. 1 depicts a basic embodiment of the invention. A radiation source catheter or wand 100 has a radiation source 101 at its distal end. The catheter or wand 100 is shown assembled within a shaft 200 of an applicator 208. The shaft 200 comprises a tubular body with a balloon 300 at its distal end 205. The distal end of the shaft 200 is bonded to the balloon at its distal extremity, and bonded to the balloon proximal extremity at 206.

At the proximal end 207 of the shaft 200 is a conventional applicator hub (not shown) as is common in radiation applicators, including a port 201 for balloon inflation fluid in communication with a fluid outlet 202 within the balloon, and a seal receptacle 203 for an O-ring 204. The O-ring 204 maintains a movable seal between the shaft 200 and the catheter 100 in this embodiment, allowing both rotation and translation of the catheter within the shaft without loss of balloon inflation pressure.

Figure 2:
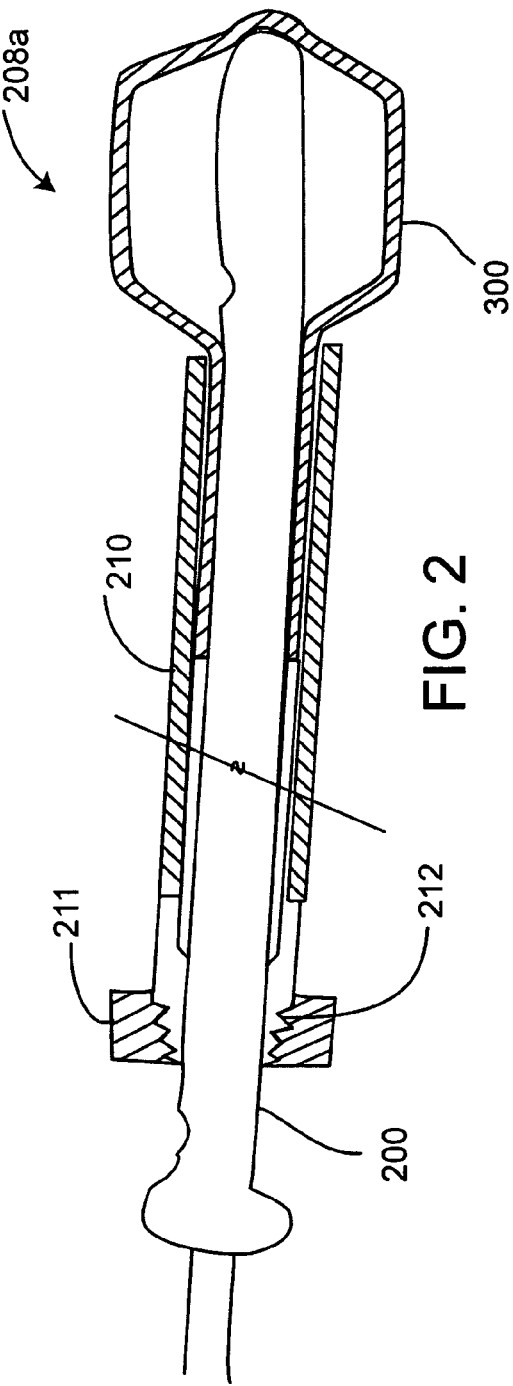
FIG. 2 is a side view in cross-section of an applicator of the invention, including a slidable tubular sheath covering a portion of the expandable balloon, limiting its expansion.

FIG. 2 shows an optional tubular sheath 210 placed over and coaxial with the shaft 200 and proximal end of the balloon 300, on an applicator 208a.

The sheath 210 may be adjusted and positioned axially as desired along the body of the shaft 200 in order to limit the inflated length of the balloon. The sheath 210 can be held in position by a nut 211 and a tapered thread 212 at the split, proximal end of the sheath 210. When positioned as desired, the sheath 210 and nut 211 are rotated relative to one another such that the tapered thread causes the split end of the sheath to tighten onto the shaft 200. The sheath may be rigid and of metal (stainless steel, for example) or engineering plastic and flexible (PVC, Nylon). Advantageously, it may be radio-opaque (e.g. barium loaded if plastic). In an alternate embodiment (not shown) a latch can be provided on the sheath to engage with an element of the shaft or of a hub to position the sheath relative to the shaft.

The balloon 300 can be either elastic or inelastic in nature; that is, it can be of material to substantially conform to tissue, or material to form a generally rigid predefined shape. In use, the balloon preferably abuts the patient's tissue to be treated. If the nature of the cavity being irradiated is irregular or rigid, an elastic construction is usually preferred. A suitable material is silicone rubber, and of such a thickness that inflation pressure will cause expansion of the balloon to substantially fill the irregular cavity to be irradiated. If in contrast, the cavity to be irradiated is of fairly uniform geometry, or if the tissue is highly compliant, then an inelastic balloon might be preferred. Such a balloon, constructed for example of PET or polyurethane, can be fabricated to expand to a predetermined shape, and if properly proportioned, usually can deform the tissues to be treated such that they conform to the balloon geometry. A balloon that assumes a known (fairly rigid) shape has been important in use of isotope radiation, with the isotope source positioned centrally in the balloon to produce a known distance to tissue and uniform dose distribution. Such is one embodiment of this invention, and can be considered as represented in FIGS. 1 and 2, and also in FIGS. 3, 6a-6b, 7 and 8a-8b. With a controllable electronic x-ray source, however, more latitude is permitted and irregular shapes can be treated, with conforming balloons.

Generally, it is preferable that the position of the radiation source within the balloon be known as precisely as possible. Therefore, it is usually advantageous that the balloon 300 be secured to or supported on the shaft of the applicator at both distal and proximal balloon extremities. There may be situations, however, where the geometry of the anatomy to be treated and that of the balloon are sufficiently predictable that anchoring of the balloon to the shaft only at the proximal end of the balloon is adequate for proper control of therapy.

Depending on the anatomy being treated, and perhaps its surrounding anatomy, it may be preferred that the applicator be curved as shown in FIG. 3. As shown the body of the shaft 301 has a continuous curve, although the form can be arbitrary to suit the anatomy of the patient. If desired, the body of the shaft 301 can be of deformable material such as annealed stainless steel, and bent to suit by the radiation therapist. Further, it could be of Nitinol according to the catheter teachings of U.S. Pat. No. 4,665,906. Use of a flexible source catheter 100 permits the radiation source to be positioned at will along the tubular bore of the shaft 301. A situation in which a curved applicator is preferred is shown in FIG. 8b and discussed below.

The preferred radiation source of this invention is a miniature x-ray tube 101, positioned at the end of a cable catheter or wand 100. An example of such an x-ray source is described in U.S. Pat. No. 6,319,188. Generally, they consist of a flexible, high-voltage cable (as part of the catheter 100) connected to a power source and controller at its proximal end and to the small x-ray tube at its distal end. The x-ray tube has a cathode which can be caused to emit electrons (for example by heat) at its proximal end and a target anode at its distal end. The voltage between the cathode and electrode accelerates the electrons emitted by the cathode such that they impact the anode creating x-rays. The spectrum of energies produced is related to the voltage applied between the anode and cathode and the target material used. It is this anode to cathode high voltage (as well as current control) that provides the option for control of the radiation emitted from such an x-ray device as compared to a radio-isotope source which always emits in a known and unchangeable manner.

The shape of the anode, and its structure and shielding, determine the directionality of the x-rays emitted. They may be omni directional, or may be directed radially or axially, or a combination thereof. Anode shaping is well known by those skilled in the art of x-ray generation apparatus. The penetration of the x-rays in tissue is directly related to the voltage accelerating the electrons, and the cumulative dose may be controlled by x-ray source beam current or dwell time at positions within the body of the patient. Current can be varied in the tube to control cathode emission. It should also be noted that dosimeters can be placed on the balloon at plural locations, thus to be directly adjacent to the tissue, and can sense dose from the source so that the dose being delivered to different tissue regions being treated is known. This enables control of dose delivered to all regions in an irregularly-shaped cavity and balloon; feedback control is disclosed in copending application Ser. No. 10/464,140, incorporated herein by reference.

Figures 4A, 4B, 4C:
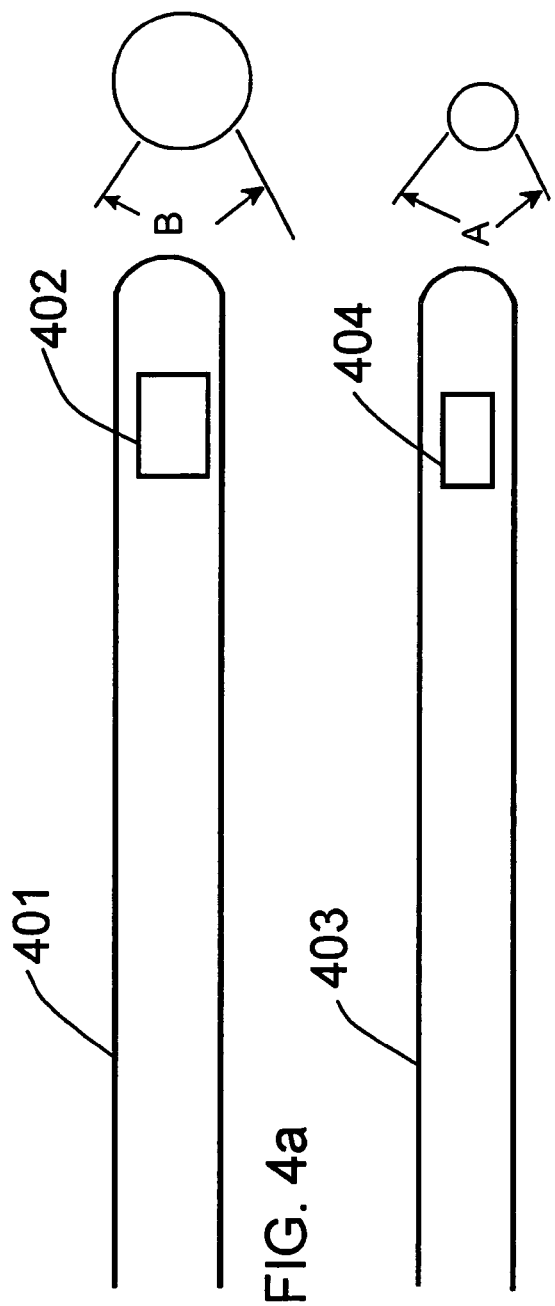
FIG. 4a is a side elevation view of a radio opaque outer element of a source guide with a window through which radiation may be directed.
FIG. 4b is a side elevation view of the inner element of a radio-opaque source guide with a window through which radiation may be emitted.
FIG. 4c illustrates how the source guide elements can be assembled and how the window depicted in FIGS. 4a and 4b may be adjusted to cooperate in obtaining a desired window through which a controlled beam of radiation is to be emitted.

On occasion, it is preferable to shape the emission field of the x-ray tube by shielding the output of the source 101 rather than by anode design. An example of such shielding is illustrated by a directional source guide 400 in FIGS. 4a-c. The directional source guide 400 is inside the lumen of an applicator shaft. FIG. 4a shows in side elevation the outer, tubular, radio opaque shield sleeve 401 having one closed end and a window 402 which is open for an arbitrary length and an arc B. FIG. 4b shows an inner, tubular, radio-opaque sleeve 403 having one closed end and a window 404 which is open for an arbitrary length and an arc A. The inner bore of the shield sleeve 401 accommodates the outer diameter of sleeve 403. The outer diameter of the sleeve 401 is accommodated by the inner diameter of the shaft 200 and the O-ring seal 204, if the applicator is constructed as in FIG. 1. The inner bore of the smaller sleeve 403 accommodates the source catheter 100. When the inner and outer sleeves 401 and 403 are assembled, they comprise the source guide 400 shown in FIG. 4c. Windows 402 and 404 may be positioned rotationally and axially to create a clear window 405 of arbitrary size for desired radiation emission as shown in FIG. 4c. This composite window 405 may then be directed toward the tissue to be irradiated. The relative positions of sleeves 401 and 403 may be fixed by a tapered thread and nut similar to that shown in FIG. 2, as may the inner sleeve 403 in relation to the source catheter body 100. Positioning and movement of the source catheter and of the source guide sleeves 401 and 403 can be controlled by a program driven machine. With this source guide, stray radiation is eliminated, protecting healthy tissue or tissue especially susceptible to radiation damage, such as the bowel. Such a source guide may be fashioned from barium loaded engineering plastic. Note that intermediate elements between the source catheter and the shaft may necessitate additional seals to prevent inflation fluid leaks, depending on the nature of the inflation port.

Directionality and control of the position at which radiation is directed can be achieved in other ways. For example, the x-ray 101 source within the catheter 100 can simply be shielded by a radio opaque shield or coating on the x-ray tube or surrounding catheter, allowing radiation to be emitted only in a single cone or shaft, and the axial position and rotational orientation of the catheter can be manipulated in a selected pattern of movement so as to place the proper dose at each region of the tissue.

FIG. 5 depicts an embodiment of an applicator 505 in which a base portion 506 of the applicator terminates near the proximal end of the balloon 300, and a cupped, separate element or bearing 500 is affixed to the distal extreme of the balloon 300, for example by bonding. A shaft or source guide 501 has a branch 502 forming a curved guide lumen, closed at its distal end, and an axial extension 503 to cooperate with the cup 500 to maintain the position of the shaft or source guide 501 relative to the distal end of the balloon. If necessary to maintain axial position of the cup 500 relative to wand guide 501, a groove 504 (shown in alternate detail, FIG. 5a) can be provided in the axial extension 503 into which the rim of the cup 500 can be heat formed after assembly of the shaft 501 into the base member 506. The guide 501 can be rotated within the shaft 200 such that the branch describes a circle within the balloon 300, directing radiation outward in a conical or radial manner, when the source catheter is in the branch. Such a construction would be useful in directing axial radiation into the fornices of the vagina, or for irradiation of such tissue alongside the site of hysterectomy.

FIG. 5b shows another embodiment wherein the shaft 501 is not rotatable but has two branches 502 and 507 into which the source can be placed. Here the end of the shaft 501a is fixed to the balloon. This forked shaft 501a can have the two branches or forks 502 and 507 at 180° or at any other selected angle, to protect, for example, the bladder and bowel by providing selected directional radiation. The source catheter (not shown) can have a slight bend near its tip so it can be steered into one channel (502, 507), then the other.

The applicator embodiment 607 of FIGS. 6a and 6b comprises an optional vacuum channel to evacuate exudate or other fluids from the region near the distal end of the balloon 300 through a port 605 in response to vacuum drawn on a port 606 at the proximal end of a multiple-lumen shaft 600. Exudate or fluid is drawn through an annular passage 604 between the catheter 100 and the shaft 600's inner diameter. The ports 605 and 606 communicate through this annulus. To provide inflation of the balloon, a lumen 601 is provided in the wall of the shaft 600, terminating at a port 603 within the balloon, and at inflation port 602 near the proximal end of the shaft 600.

Figure 7:
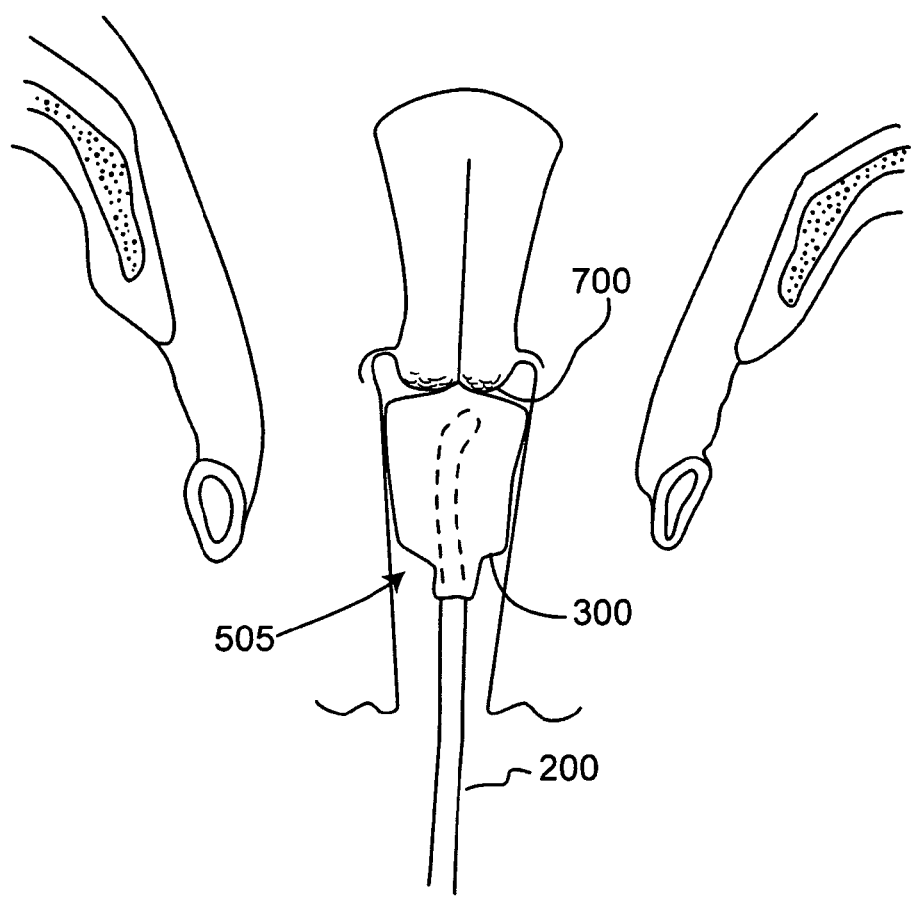
FIG. 7 shows a portion of a patient's vaginal anatomy in coronal section with early stage cancer (shaded) at the mouth of the cervix. An applicator of the invention positioned within the vagina.

A preferred method of use of the invention apparatus is illustrated in FIG. 7. FIG. 7 shows in frontal coronal section the applicator 505 of FIG. 5 in the vaginal space of the patient, positioned to treat early stage cancer at the mouth of the cervix 700, the cancer being indicated by shading near the distal end of the applicator. In use, the deflated applicator 505 is inserted into the vagina. The source catheter 100 is then inserted into the applicator, and the balloon is inflated, anchoring the applicator in position in the vagina. The controller and power supply (not shown) are connected to the source catheter 100 (also not shown), and switched on. Then treatment proceeds. After treatment is concluded, the system is switched off, the balloon deflated, and the applicator removed.

The treatment plan is prescribed by the physician prior to application of radiation. If therapy is to be x-ray in nature, the plan may comprise specification of dose intensity, penetration and dwell of the radiation source by position from which radiation will be emitted and the direction of emission or shielding utilized to protect healthy anatomy. Therapy may also include verification of dose delivered and feedback from sensors placed near the anatomy being treated, as noted above, on or in the applicator, or on external anatomy of the patient or at interstitial positions. Preparation of a plan of this sort and subsequent treatment to plan are discussed thoroughly in copending application Ser. No. 10/464,140, filed Jun. 18, 2003.

Figure 8A:
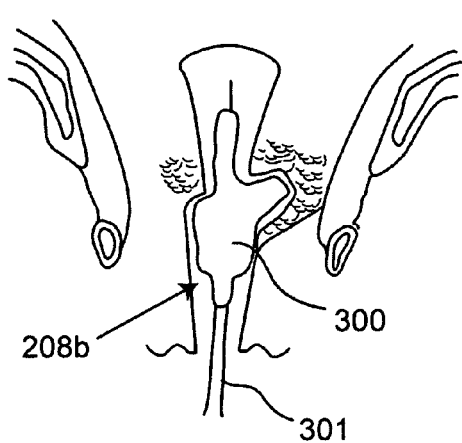
FIG. 8a shows the patient's anatomy with advanced cancer in coronal section with an applicator of the invention positioned within the vagina and partially into the uterus.
Figure 8B:
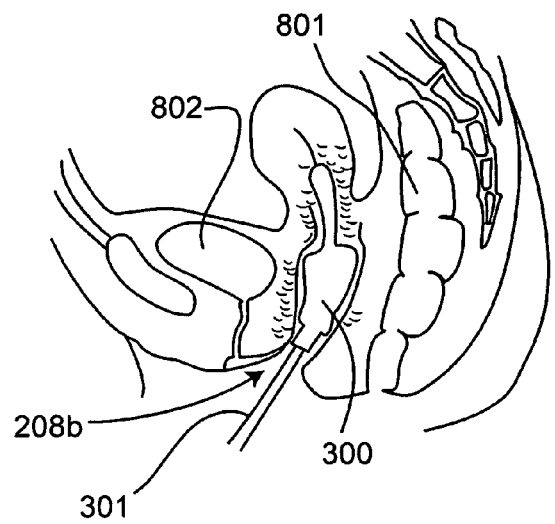
FIG. 8b shows the anatomy of FIG. 8a in medial sagittal section, again with an applicator within the vagina and a portion of the uterus.

A further illustration of the use of apparatus of the invention is shown in FIGS. 8a and 8b. FIG. 8a is a frontal coronal section through the vagina showing later stage cancer with involvement of the uterus and pelvic structure to the patient's left of the vagina. FIG. 8b shows a sagittal section of the anatomy to be treated. The inflated, curved applicator 208b of FIG. 3 is shown positioned in the vagina, and partly into the uterus. In use, the cervix is dilated and the applicator is properly positioned. The source catheter is then inserted and the balloon 300 inflated to abut the tissue and substantially fill the space around the radiation source, anchoring the applicator. The controller and power supply (not shown) are connected to the source catheter 100, and switched on. Then treatment proceeds. After treatment is concluded, the system is switched off, the balloon deflated, and the applicator removed.

Another embodiment of the applicator of the invention, not illustrated, can have a balloon with a generally elliptical cross section, short front-to-back and shielded at front and back ends to protect the bowel and bladder, which are indicated at 801 and 802 in FIG. 8b.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. An applicator for delivering ionizing radiation for intracavity brachytherapy of the vagina and proximity, comprising:
    an inflatable balloon, with a shaft that extends into the interior of the balloon,
    the shaft having a conduit for inflating the balloon by admitting fluid to the interior of the balloon,
    the shaft also being capable of receiving a source of ionizing radiation for delivery of radiation, and
    adjustment means for adjusting the length of an inflated portion of the balloon, comprising a slidable sheath that slides axially relative to the balloon, covering a desired length portion of the balloon from its proximal end so as to limit expansion of the balloon to a remaining portion distal to and not covered by the sheath,
    whereby the balloon on the shaft can be placed in a vaginal cavity with the balloon deflated, with adjustment made via the adjustment means, and, with the balloon inflated and the ionizing radiation source in the shaft, the applicator can be used to irradiate a selected region of tissue.

2. The applicator of claim 1, wherein the balloon is formed of elastic material so as to generally conform to tissue.

\* \* \* \* \*